(12) United States Patent
Lestelle et al.

(10) Patent No.: US 10,274,444 B2
(45) Date of Patent: Apr. 30, 2019

(54) DEVICE FOR RESISTIVE MEASUREMENT OF THE MOISTURE OF A POROUS MINERAL MATERIAL, AND APPLICATION TO WATER MONITORING OF PLANTS

(71) Applicant: Dominique Lestelle, Paris (FR)

(72) Inventors: Dominique Lestelle, Paris (FR); Robert Boden, Dourdan (FR)

(73) Assignee: Dominique Lestelle, Paris (FR)

( * ) Notice: Subject to any disclaimer, the term of this patent is extended or adjusted under 35 U.S.C. 154(b) by 0 days.

(21) Appl. No.: 15/395,387

(22) Filed: Dec. 30, 2016

(65) Prior Publication Data
US 2017/0191951 A1 Jul. 6, 2017

(30) Foreign Application Priority Data

Dec. 30, 2015 (FR) ..................................... 15 63476
Dec. 29, 2016 (FR) ..................................... 16 63524

(51) Int. Cl.
| | |
|---|---|
| *G01N 27/04* | (2006.01) |
| *A01G 9/02* | (2018.01) |
| *A01G 27/00* | (2006.01) |
| *A01G 27/06* | (2006.01) |
| *G01N 33/00* | (2006.01) |
| *G01N 33/24* | (2006.01) |

(52) U.S. Cl.
CPC ............. *G01N 27/048* (2013.01); *A01G 9/02* (2013.01); *A01G 27/005* (2013.01); *A01G 27/06* (2013.01); *G01N 33/0098* (2013.01); *G01N 33/246* (2013.01)

(58) Field of Classification Search
CPC ....... G01N 33/0098; A01G 9/02; A01G 27/06
See application file for complete search history.

(56) References Cited

U.S. PATENT DOCUMENTS

| | | | | |
|---|---|---|---|---|
| 2,740,032 | A | | 3/1956 | Bouyoucos |
| 4,478,975 | A | * | 10/1984 | Dessaint ............. C04B 41/4842 524/871 |
| 4,531,087 | A | * | 7/1985 | Larson ................... G01R 27/02 324/696 |

(Continued)

FOREIGN PATENT DOCUMENTS

| | | |
|---|---|---|
| DE | 10 2013 018917 A1 | 5/2015 |
| FR | 12 01210 A | 12/1959 |

(Continued)

OTHER PUBLICATIONS

Search Report and Written Opinion as issued in French Patent Application No. 1563476, dated Aug. 25, 2016.

*Primary Examiner* — Giovanni Astacio-Oquendo
*Assistant Examiner* — Alvaro Fortich
(74) *Attorney, Agent, or Firm* — Pillsbury Winthrop Shaw Pittman LLP

(57) ABSTRACT

A device for resistive measurement of the moisture of a material, which is mineral, rigid and which has open porosity, the device including a block of material of which it is desired to measure the resistance variations as a function of its water content, at least two detection electrodes which are rigid, non-oxidising and bare, applied parallel against the material, and sealed on to the latter by a blend of powder of material and lime, wherein each detection electrode is connected to an electronic unit able to generate a measuring current and an electronic unit able to measure the resistance between the said electrodes.

16 Claims, 4 Drawing Sheets

(56) References Cited

U.S. PATENT DOCUMENTS

Figure 1:
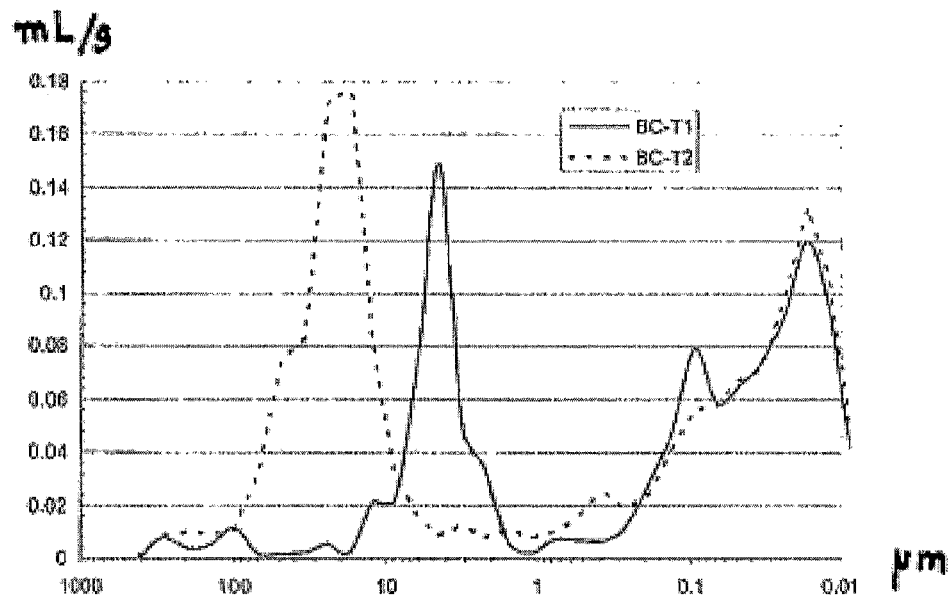

| | | | | |
|---|---|---|---|---|
| 5,439,566 A | * | 8/1995 | Zucker | C02F 1/34 |
| | | | | 204/222 |
| 8,257,487 B2 | * | 9/2012 | Ludwig | C04B 22/064 |
| | | | | 106/713 |
| 2001/0027275 A1 | * | 10/2001 | Meredith | A61B 5/0534 |
| | | | | 600/547 |
| 2006/0113537 A1 | * | 6/2006 | Krulevitch | B81C 1/0023 |
| | | | | 257/57 |
| 2007/0204580 A1 | * | 9/2007 | Kunieda | B01D 39/2075 |
| | | | | 55/523 |
| 2010/0058835 A1 | * | 3/2010 | Seo | G01N 27/223 |
| | | | | 73/29.02 |
| 2011/0223338 A1 | * | 9/2011 | Mertens | C04B 28/146 |
| | | | | 427/383.1 |
| 2011/0311308 A1 | * | 12/2011 | Brouillette | B01F 3/12 |
| | | | | 404/75 |
| 2013/0196070 A1 | * | 8/2013 | LeFevre | C04B 26/02 |
| | | | | 427/385.5 |
| 2014/0069170 A1 | * | 3/2014 | Seo | G01N 27/121 |
| | | | | 73/29.05 |
| 2014/0088522 A1 | * | 3/2014 | Nuzzo | A61H 7/005 |
| | | | | 604/290 |
| 2016/0313271 A1 | * | 10/2016 | Raupach | G01N 27/048 |

FOREIGN PATENT DOCUMENTS

| | | |
|---|---|---|
| FR | 2 986 328 A1 | 8/2013 |
| FR | 2986328 * | 8/2013 |
| FR | 2 988 262 A1 | 9/2013 |
| FR | 2988262 * | 9/2013 |
| FR | 2 996 101 A1 | 4/2014 |

* cited by examiner

DEVICE FOR RESISTIVE MEASUREMENT OF THE MOISTURE OF A POROUS MINERAL MATERIAL, AND APPLICATION TO WATER MONITORING OF PLANTS

CROSS-REFERENCE TO RELATED APPLICATIONS

This application claims priority to French Patent Application No. 1663524, filed Dec. 29, 2016 French Patent Application No. 1563476, filed Dec. 30, 2015, the entire contents of which are incorporated herein by reference in its entirety.

The invention concerns a device for resistive measurement of the moisture of a porous material M with open porosity. It also concerns its application to a device for measurement of the moisture of a granular or pulverulent material, or alternatively to a plant culture substrate of which it is desired to measure the moisture, when it is brought into contact and in water balance with this material M instrumented according to the invention. Finally, by placing the said device for measuring moisture close to the roots of plants and on the water inflow path, a device for monitoring a plant's water consumption is obtained.

Devices for resistive measurement of the moisture of a porous material M have long been known for their simplicity and their low cost. It should be noted that for the measurement of the moisture of granular or pulverulent materials, they provide an inexpensive alternative to capacitive measurements. Capacitive measurements place two parallel electrodes in the said material to measure the dielectric constant of the material separating them. These electrodes are excited by an alternating current of the order of several tens of kHz to several hundreds of kHz. But a problem arises from the fact that the grains of this material also have a degree of resistance, between which there are many contact resistances. The injected alternating current is distributed between the condenser and many ohmic resistors in parallel, which are subject to sudden or even alternating variations (if vibrations are present).

The simplest technique for resistive measurement could thus become advantageous again provided the problem posed by the existence of contact resistances which are difficult to control is resolved. Indeed, between the two measuring electrodes in reality there is not a single resistance (that of material M), but three such resistances. The first is the contact resistance between the first electrode and this material M, the second is the resistance of material M, and the third is the contact resistance between this material M and the second electrode. And a contact resistance varies substantially depending on many factors, such as the local microroughness of the materials used, the elasticity of the parts in contact (the areas of the electrodes in contact with material M), and the pressure between the conducting elements in contact (in this case the electrodes and material M).

According to the prior art FR2 986 328 of 31 Jan. 2012 (CEMAGREF), material M is a porous synthetic matrix, in water balance in the middle of a culture substrate, into which two electrodes are planted. However, the described device has two major disadvantages.

The first disadvantage derives from the fact that the synthetic material used accomplish water balance has an insufficiently uniform distribution of pore diameters. And this uniformity determines the ability to measure uniformly all the suction tensions, which is equivalent to saying all the moisture values. Indeed, it is known that there is a negative suction pressure required to extract the water from the said void or pore for every diameter of a porous void (and thus for every a capillary void), as mentioned in Table 1 below, which shows the relationship between the size of the pores and the suction tension required to empty them of their water. The three values (in italic, with asterisks) mentioned in FR2 986 328 have been added by interpolation to this table produced by ROWELL in 1994

TABLE 1

| Size of pores (μm) | Suction tension (hPa = mbar) | Note |
| --- | --- | --- |
| 20,000 | 0.15 | large crevice |
| 4,000 | 0.75 | worm trail |
| 300 | 10 | diameter of a wheat root |
| 60-30 | 50-100 | Suction tension at capacity in the field |
| 32 | 850* | Ceramic |
| 2 | 1,500 | limit of pore containing water which is easy to use |
| 1.6 | 2,000* | Plaster |
| 0.57 | 5,000* | value sought by FR2 986 328 |
| 0.2 | 15,000 | Wilting point |
| 0.003 | 1,000,000 | Suction tension of a dry soil exposed to air |

This means that the mercury porosimetry curve, in the range 3.2 μm to 0.57 μm, and if possible outside it, must be as constant as possible in order for the measuring device to react identically to all suction tensions; failing this it must be monotonic and have as regular a gradient as possible to allow corrections.

Figure 2:
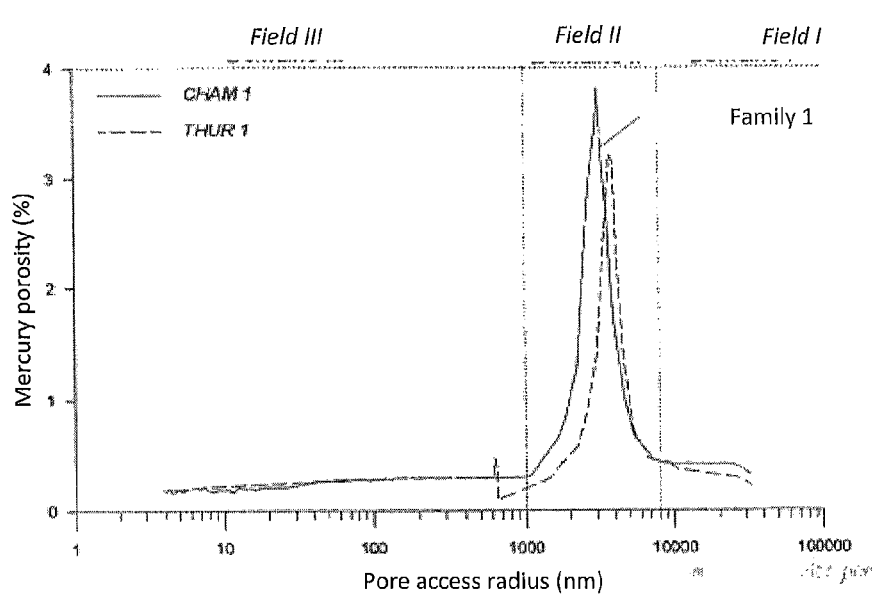

FIG. 1 reproduces FIG. 2 of FR2 986 328, which "is a graphic representation of the incremental intrusion of the mercury as a function of the diameter of the pores (mercury porosimetry)". Table 2 summarises, for each reference diameter, the mL/g values corresponding to the quantity of pores available with the diameter in question.

TABLE 2

| | diameter of pores (μ) | suction tension (hPa) | porosity for material T1 (mL/g) | porosity for material T2 (mL/g) |
| --- | --- | --- | --- | --- |
| ceramic | 3.2 | 850 | 0.145 (Max.) | 0.008 (min.) |
| plaster + clay | 1.6 | 2,000 | 0.036 | 0.0079 (min.) |
| ∅ minimum | 0.57 | 5,000 | 0.07 | 0.015 |

A pronounced peak of sensitivity is observed for certain pore diameters. For T1 at 4 μm, 0.1 μm and 0.013 μm, and for T2 at 20 μm, 0.25% m (less pronounced) and 0.013 μm. The amplitude ratios can be substantial, ranging in the case of T1 from approximately $6.10^{-4}$ to 145 (i.e. a large difference of the ability to absorb the surrounding moisture, of the order of 217,000) and in the case of T2 of the order of 0.01 to 178, i.e. a difference of the order of 178. These curves are also highly monotonic, which has a major adverse effect on any attempt to linearise them.

More generally, the product presented as the matrix able to achieve water balance is produced synthetically from cement, plaster, sand, lime and Al. And these materials consist of powders with precise granulometries. The pores of the resulting material will consequently also have relatively repetitive dimensions, creating a peak of sensitivity for the pore diameter (and therefore the suction tension) associated with each of the constituents. When, for example, the authors of FR2 986 328 increase the proportion of aluminium to extend the measuring range, they increase the amplitude of the peak corresponding to the diameter of the voids between the aluminium grains. They obtain a degree of extension of the measuring scope, but only at the cost of an increasing non-linearity.

The second disadvantage of FR2 986 328 derives from the manner of "placing" the electrodes in the porous matrix. Everything suggests that they are inserted forcefully after the matrix, preferably produced in an autoclave, is manufactured (p. 3 line 3). Firstly, the difference of heat conductivity between electrodes, which are very efficient heat conductors, and a porous cement which is a relatively good insulator would create temperature non-uniformities causing the matrix to crack or split. And, secondly, no binder able to produce a seal is mentioned. The electrodes are therefore in electrical contact with the matrix via contact resistances which are proportional to the pressures with this matrix.

To address these problems the device for resistive measurement of moisture according to the invention contains a material having constant porosity in a wide range of pore diameters, and electrodes which are connected to it in a way in which fluctuations of contact resistances have no effect on them.

DESCRIPTION OF THE INVENTION

To accomplish this, the device according to the invention contains a block of material M in its basic conversion and a device comprising:
- a block (1) of a material M which is mineral and rigid with an open porosity, and of which it is desired to measure the resistance variations as a function of the water content
- at least two detection electrodes (2) and (2') which are rigid, non-oxidising and bare, applied parallel against the said material M, and sealed on to the latter by a blend of powder of material M and lime where each electrode (2) and (2') is connected to an electronic unit (3) able to generate a measuring current i and an electronic unit (4) able to measure the resistance between the said electrodes.

Preferentially, material M is a natural material with open porosity, the distribution of the diameters of which is continuous between 10 and 10,000 nm (0.01 to 10 µm). Its mercury porosity curve shows a single peak in this interval, and either side of this peak is monotonic and has no extrema.

Even more preferentially, in order to prevent material M having the problems of materials produced from powders, material M is a chalky soft rock with open porosity, the distribution of the diameters of which is continuous between 10 and 10,000 nm (0.01 to 10 µm) and the mercury porosity curve of which shows a single peak in this interval, and where the binder which seals the electrodes with material M is a powder blend of M and lime, containing between 5 and 50% lime, which provides satisfactory electrical conductivity, and free circulation of moisture. It should be mentioned that the notion of "chalky soft rock" is very wide, and covers a large number of products the vast majority of which do not have the characteristics required for the invention. To implement the invention with such a component a quarry must be sought which has the rare characteristics among chalky rocks mentioned at the end of the phrase, namely "open porosity", but above all "the distribution of the diameters of which is continuous between 10 and 10,000 nm (0.01 to 10 µm)", and "the mercury porosity curve of which shows a single peak in this interval, and either side of this peak is monotonic and has no extrema". These characteristics are very foreign to the general structure of a chalky rock, but the very large number of chalky rocks available makes this search relatively easy, and the sources of supply numerous. There is no intention in the present document to list all the quarries across the planet which produce a rock meeting the criteria of the invention, and each country will find its own without any difficulty. A very advantageous example is given in the paragraph below, which is in no way restrictive.

Even more preferentially, this chalky soft rock is Tuffeau, the porosity of which is continuous between 3 and 30,000 nm. By way of example, FIG. 2 shows two examples of Tuffeaus which satisfy the criteria of the invention (D. Dessandier, Tours University Thesis "Study of the porous environment and the fluid transfer properties of white Touraine Tuffeau", 23 Jun. 1995). This does not mean that all Tuffeaus satisfy it, but that there is a high probability of finding the characteristics of material M in Tuffeaus.

In addition to these previous conditions, it is advantageous to choose a material M which has a surface specific area of at least 10 $m^2/g$. Among the Tuffeaus this is generally found in the rocks containing at least 5% of smectite.

LIST OF FIGURES

FIG. 1 reproduces FIG. 2 from prior document FR2 986 328.

Figure 2B:
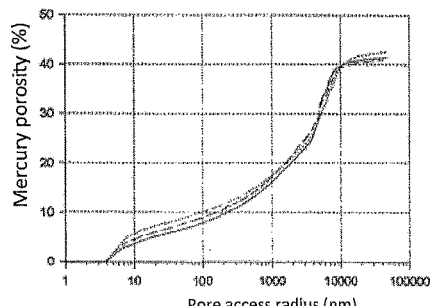
Figure 2C:
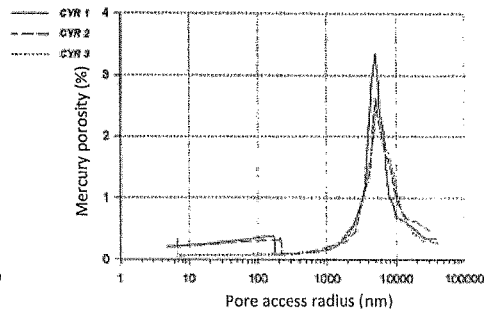

FIG. 2A, taken from the above-mentioned Thesis of D. Dessandier (p. 49), gives a first idea of the habitual pore distributions in white Tuffeau; FIGS. 2B and 2C (cf. Thesis p. 243) show the mercury porosimetry results of two particular types of Tuffeau. In 2A the number of pores for each diameter can be seen, and in 2B the proportion of pores with the diameter in question.

Figure 3:
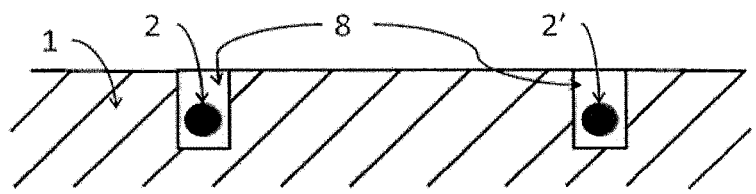

FIG. 3 shows a detail of the installation of wire electrodes (2, 2') in block (1) of material M, with the presence of the binder (8) producing the seal.

Figure 4A:
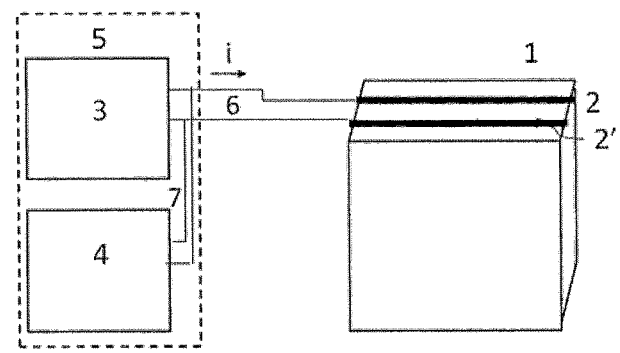
Figure 4:
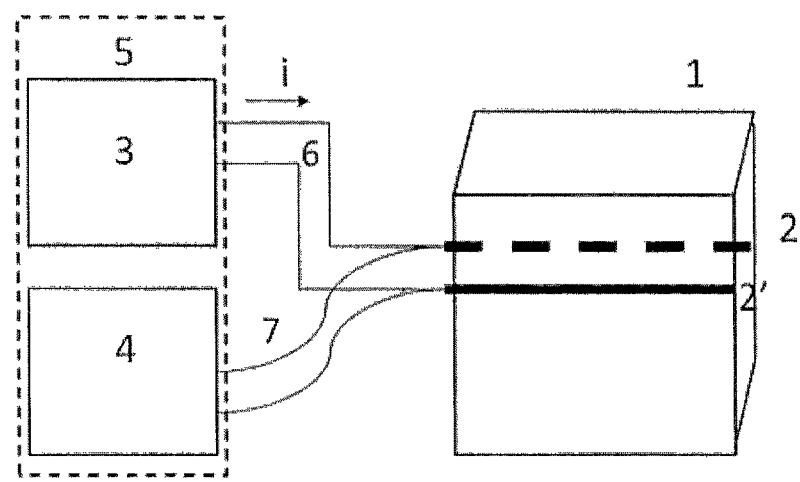

FIG. 4 A shows an embodiment of the invention in which the electrodes (2, 2') are sealed in the same side of the block (1) of material M, and FIG. 4B an embodiment in which they are sealed in opposite sides of the block (1).

Figure 5:
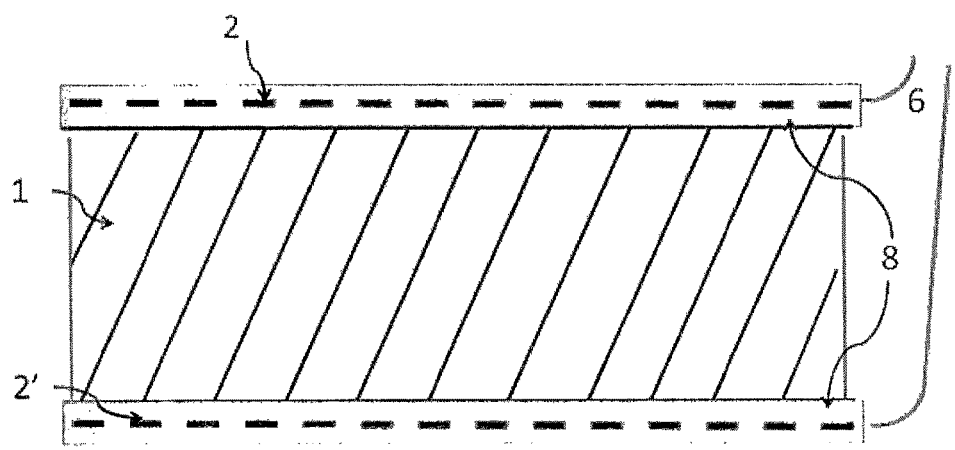

FIG. 5 shows an embodiment of the invention intended to be immersed in a granular or pulverulent material, and able to form a tensiometer.

Figure 6A:
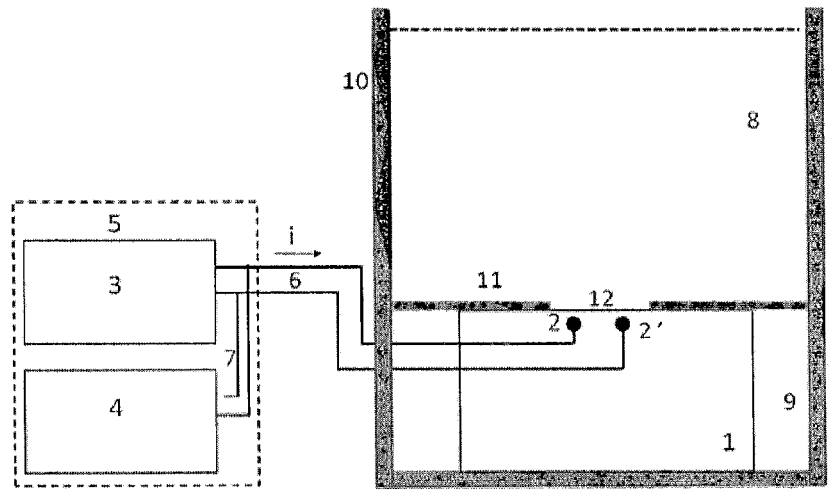
Figure 6B:
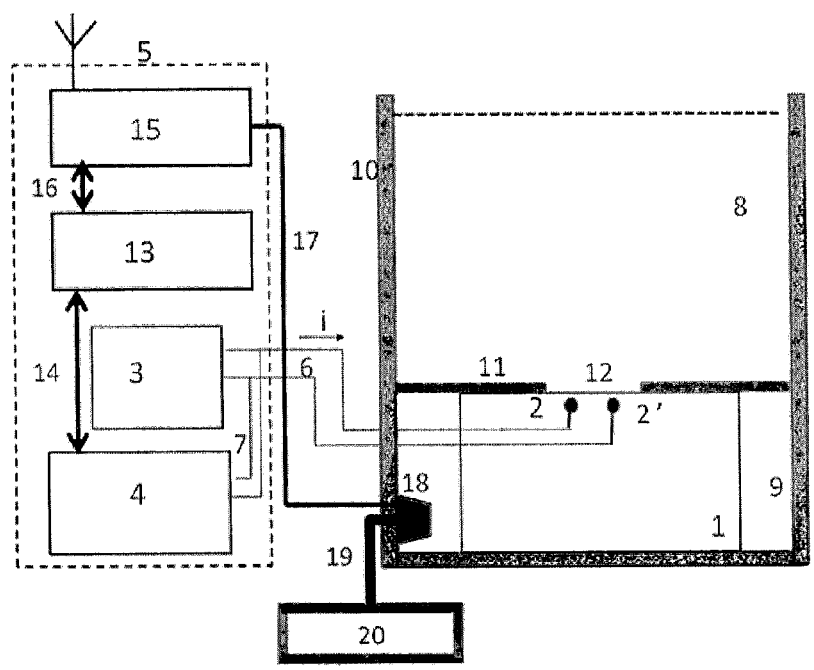

FIG. 6 A shows an embodiment in accordance with FIG. 4A installed in a specific container (10) for plants, in order to accomplish water monitoring of plants, and FIG. 6 B is completed by additional electronic modules making the assembly autonomous (by water-filling being activated by a drying condition) and/or communicating.

DESCRIPTION OF PREFERENTIAL EMBODIMENTS

According to a first embodiment, material M was chosen from among the Tuffeaus satisfying the characteristics of the invention. There are two rectilinear electrodes, each consisting of a stainless steel rod measuring 3 to 6 mm in length, placed in a groove made in the Tuffeau, with a diameter approximately 1 mm greater than the diameter of the stainless steel rod, 1.5 to 2 times deeper than this diameter, where both rods are parallel and placed in parallel grooves in accordance with FIG. 3. It would not be outside the scope of the invention to place three parallel rods, where the first and the third are connected together to constitute one of the electrodes (2), and the second constitutes the other electrode (2'). The binder (8) of the seal is made as described above by a blend of powder of material M and a proportion of lime of between approximately 5 and 50%, depending on the desired performance.

The assembly of the device according to the invention is represented diagrammatically in FIG. 4, according to two embodiments. According to a first embodiment represented diagrammatically in FIG. 4 A, the invention includes electrodes (2, 2') sealed parallel to one another, side-by-side, in the same side of the block (1) of material M, and connected by a pair of conductors (6) to an electronic unit (3) able to generate a measuring current. They are chosen to be rectilinear, but it is self-evident that they cannot be rectilinear without going beyond the scope of the invention. The voltage conveying the resistance information is then sampled by the conductors (7) leading it to electronic unit (4), which can make this measurement. The assembly (5) of electronic units (3) and (4) constitutes an electronic conditioner which can use the blocks (1) of material M holding at least two sealed electrodes, according to the invention. It is self-evident that electronic unit (3) could generate a constant voltage, and electronic unit (4) could measure the current resulting from it, bearing in mind the resistance between the electrodes (2, 2'). Such a configuration is equivalent to the previous one for those skilled in the art.

According to a second embodiment represented diagrammatically in FIG. 4 B, the invention includes rectilinear electrodes (2, 2') sealed in parallel as above, but in two opposite faces of the block (1) of material M. They are in principle positioned facing one another so as to minimise the thickness of material M which the current must traverse, several pairs or an uneven number of electrodes could equally well be positioned in staggered rows. The other elements with the same marks are identical to the first embodiment, and will not therefore be repeated.

According to a variant of this second embodiment, which will be called the third embodiment, block (1) is made thinner in the dimension separating the sides bearing the electrodes. For information, this dimension is generally within a range of between several mm and approximately four cm, depending on the range of measurements which it is desired to make. The said electrodes (2, 2') are then non-oxidising grids which allow moisture to pass, sealed in parallel on to both opposite sides of the block (1) by the binder (8) mentioned above, which allows electrical conduction and passage of moisture. The assembly then forms a sort of sandwich which can be immersed in a pulverulent or granular material, the moisture of which it is desired to measure, provided this material is indeed in contact with the block (1), and provided that a sufficient period has been allowed for the water balance to be established. When dipped in a culture substrate, such an implementation according to this third embodiment of the invention constitutes a tensiometer to measure the water content of the soils.

According to a variant of the first embodiment, which will be called the fourth embodiment, a device according to FIG. 4A is incorporated in a plant container with a water reserve, in accordance with the object of patent application FR 12 01210 of the 24/04/12, issued in October 2016. The result is represented diagrammatically in FIG. 6 A. Such a container (10) contains an upper compartment which can contain earth or a culture substrate (8), separated by a base (11) from a lower compartment (9) which can receive a water reserve. A block (1) of material M allows the water to rise by capillarity when water is present in the reserve (9), in order to be distributed to the roots of the plants passing through a hole (12) made in the plate (11). In a second phase which starts when all the water in this reserve has been used up, the block (1) is emptied in a manner which varies over time, and depending on the suction tension of the plants placed in the top of the substrate (8). This manner is very close to the water behaviour of a perfect ground bed, which gradually changes the metabolism of these plants to water conservation mode.

This embodiment can also be defined as a measuring device according to the first embodiment in which the electrodes are parallel side-by-side on the same side of the block (1), where the said block (1) is incorporated in the base of a plant container (10) including an upper compartment which can contain a culture substrate (8), separated, by a base (11) with a hole (12), from a lower compartment (9) which can contain a water reserve, characterised in that the block (1) of material M is able to raise by capillarity any water in the lower compartment (9) to distribute it through the hole (12) to plants in the substrate (8), and characterised in that the electrodes (2, 2') are positioned perpendicular to any water flow from the block (1) towards hole 12.

Installing the invention in the block (1) of material M accomplishing this double hydration function is extremely advantageous, and allows the plant(s) to be monitored. Such device may be completed by an on-board computer, and be developed towards an autonomous and/or communicating object, represented schematically in FIG. 6B. A computer embedded in a circuit (13) with a microcontroller enables the water situation to be analysed, and actions to be generated which make operation autonomous. For example, activation according to a dryness criterion, via a wire (17) of a water pump (18), allowing the water reserve to be refilled via a pipe (19) dipped into a device-independent water reserve (20), making this assembly water self-sufficient. Finally, it is easy for those skilled in the art to add a communicating system (15) to this using a data bus (16) connected to the circuit (13). This communicating circuit is represented diagrammatically with an antenna to symbolise its communicating aspect, but in reality the antenna is integrated in the electronic module (15): for this reason it has no mark in the illustration. This communication can be accomplished remotely by Bluetooth, Wifi or by means of a Sim card, to form a communicating object able to inform an operator remotely, and/or to receive a filling instruction from the said operator.

The invention claimed is:

1. A device for resistive measurement of moisture of a porous material, comprising:
    a block of said porous material which is mineral and rigid, of which it is desired to measure resistance variations as a function of the water content, and
    at least two electrodes which are rigid and non-oxidizing, the at least two electrodes being applied parallel against said porous material, and sealed on to said porous material by a blend of powder of said porous material and lime,
    wherein each electrode is connected to a first electronic unit configured to generate a measuring current and a second electronic unit configured to measure a resistance between said electrodes.

2. The measuring device according to claim 1, wherein said porous material is a natural material with open porosity, a distribution of diameters of which is continuous between 10 and 10,000 nanometers.

3. The measuring device according to claim 2, wherein said porous material is a Tuffeau, and wherein the at least two electrodes are sealed on to said porous material by a binder consisting of the blend of powder of said porous material and of lime, wherein said lime is in a proportion of between 5 and 50%.

4. The measuring device according to claim 2, wherein said porous material has a surface specific area at least equal to 10 $m^2/g$.

5. The measuring device according to claim 2, wherein the at least two electrodes are rectilinear and sealed parallel side-by-side on to a same side of the block of said porous material.

6. The measuring device according to claim 3, wherein the at least two electrodes are sealed parallel on to two opposite sides of the block of said porous material, wherein said block is made thinner in a dimension separating said sides bearing the at least two electrodes, and wherein said at least two electrodes are non-oxidizing grids allowing the moisture and the binder to pass through.

7. An assembly including the measuring device according to claim 5 incorporated in a base of a plant container including an upper compartment configured to contain a culture substrate, separated, by the base with a hole, from a lower compartment which is configured to contain a water reserve, wherein the block of said porous material is configured to raise by capillarity any water in the lower compartment to distribute the water through the hole to plants in the substrate, and wherein the at least two electrodes are positioned perpendicular to any water flow from the block towards the hole.

8. The assembly according to claim 7, further comprising electronic means making it more water self-sufficient and/or communicating.

9. The measuring device according to claim 1, wherein each of the at least two electrodes is positioned in a groove arranged in, and extending along, an external surface of the block of said porous material.

10. The measuring device according to claim 9, wherein each of the at least two electrodes is sealed in said groove with a binder formed by the blend of powder of said porous material and lime.

11. The measuring device according to claim 9, wherein each of the at least two electrodes is positioned along a same side of the block of said porous material.

12. The measuring device according to claim 1, wherein said porous material a chalky soft rock with open porosity.

13. The measuring device according to claim 12, wherein a distribution of diameters of pores forming said open porosity is between 10 and 10,000 nanometers.

14. The measuring device according to claim 1, wherein the at least two electrodes are sealed on to said porous material by a binder consisting of the blend of powder of said porous material and of lime, wherein said lime is in a proportion of between 5 and 50%.

15. The measuring device according to claim 1, wherein a binder consisting of the blend of powder of said porous material and of lime to seal the at least two electrodes on to said porous material is different from said material.

16. The measuring device according to claim 15, wherein said porous material is chalky soft rock.

* * * * *